(12) United States Patent
Rogier

(10) Patent No.: US 9,717,897 B2
(45) Date of Patent: Aug. 1, 2017

(54) MALE REFLUX VALVE

(75) Inventor: Stephen J. Rogier, Palm Harbor, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 1038 days.

(21) Appl. No.: 13/461,760

(22) Filed: May 1, 2012

(65) Prior Publication Data

US 2012/0277688 A1 Nov. 1, 2012

Related U.S. Application Data

(60) Provisional application No. 61/481,240, filed on May 1, 2011, provisional application No. 61/559,821, filed on Nov. 15, 2011.

(51) Int. Cl.
| | |
|---|---|
| *A61M 39/24* | (2006.01) |
| *A61M 39/26* | (2006.01) |
| *A61M 39/04* | (2006.01) |
| A61M 39/10 | (2006.01) |

(52) U.S. Cl.
CPC .......... *A61M 39/26* (2013.01); *A61M 39/045* (2013.01); A61M 2039/1061 (2013.01); A61M 2039/1072 (2013.01); A61M 2039/244 (2013.01); A61M 2039/2426 (2013.01); A61M 2039/2433 (2013.01); A61M 2039/2446 (2013.01); A61M 2039/2453 (2013.01); A61M 2039/261 (2013.01); A61M 2039/262 (2013.01); A61M 2039/263 (2013.01)

(58) Field of Classification Search
CPC ................ A61M 39/26; A61M 39/045; A61M 2039/261; A61M 2039/262; A61M 2039/263; A61M 2039/1072; A61M 2039/2426; A61M 2039/1061; A61M 2039/2433; A61M 2039/244; A61M 2039/2446; A61M 2039/2456; A61M 2039/246; A61M 2039/2466
See application file for complete search history.

(56) References Cited

U.S. PATENT DOCUMENTS

| | | | |
|---|---|---|---|
| 6,036,171 | A | 3/2000 | Weinheimer et al. |
| 6,299,132 | B1 | 10/2001 | Weinheimer et al. |
| 6,543,745 | B1 | 4/2003 | Enerson |

(Continued)

FOREIGN PATENT DOCUMENTS

| | | |
|---|---|---|
| EP | 12779656.3 | 11/2014 |
| WO | PCT/US12/36024 | 8/2012 |
| WO | PCT/US12/36024 | 4/2013 |

*Primary Examiner* — Laura Bouchelle
*Assistant Examiner* — Anh Bui
(74) *Attorney, Agent, or Firm* — GrayRobinson, P.A.

(57) ABSTRACT

A male reflux valve comprising a distal body portion and a proximal body portion, the proximal body portion having a male connection for connection to a female connection of an access device, a valve element operatively positioned within the distal body portion, a core operatively positioned within the distal body portion to retain the valve element into sealing engagement with the distal body portion and an actuator reciprocably retained within a generally circular cylindrical longitudinal bore of the proximal body portion in engagement with the valve element to open the valve element when engaged by the female connection of the access device.

12 Claims, 13 Drawing Sheets

(56) References Cited

U.S. PATENT DOCUMENTS

| | | |
|---|---|---|
| 6,609,696 B2 | 8/2003 | Enerson |
| 6,651,906 B2 | 11/2003 | Saidman |
| 2003/0199835 A1* | 10/2003 | Leinsing .............. A61M 39/26 604/256 |
| 2007/0225648 A1* | 9/2007 | Winsor .............. A61M 39/045 604/167.04 |
| 2009/0163878 A1* | 6/2009 | Moberg ................ A61M 5/158 604/263 |
| 2010/0004634 A1* | 1/2010 | Whitley ............. A61M 39/1011 604/537 |
| 2011/0029056 A1 | 2/2011 | Skubitz |
| 2012/0248624 A1 | 10/2012 | Endo |

\* cited by examiner

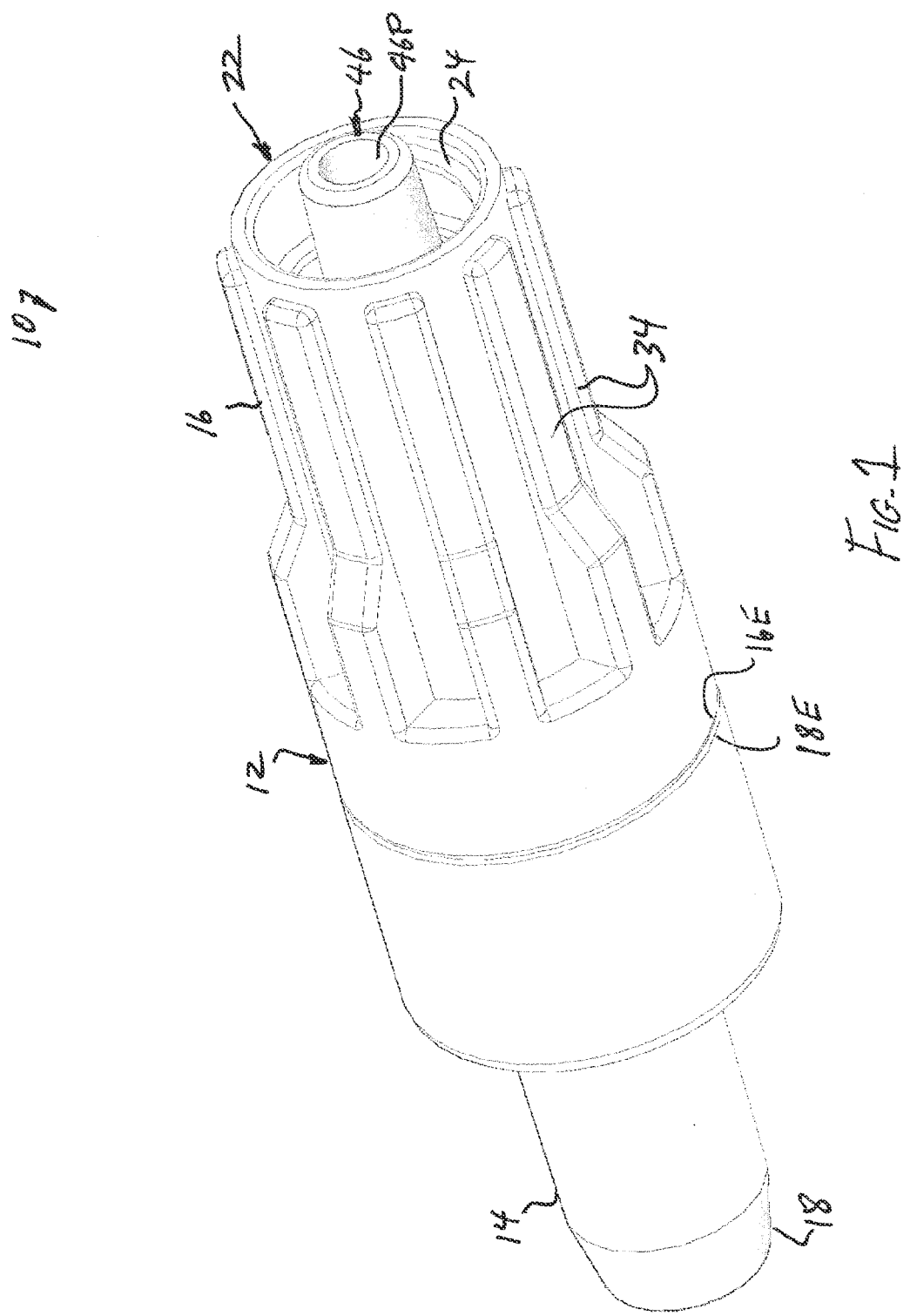

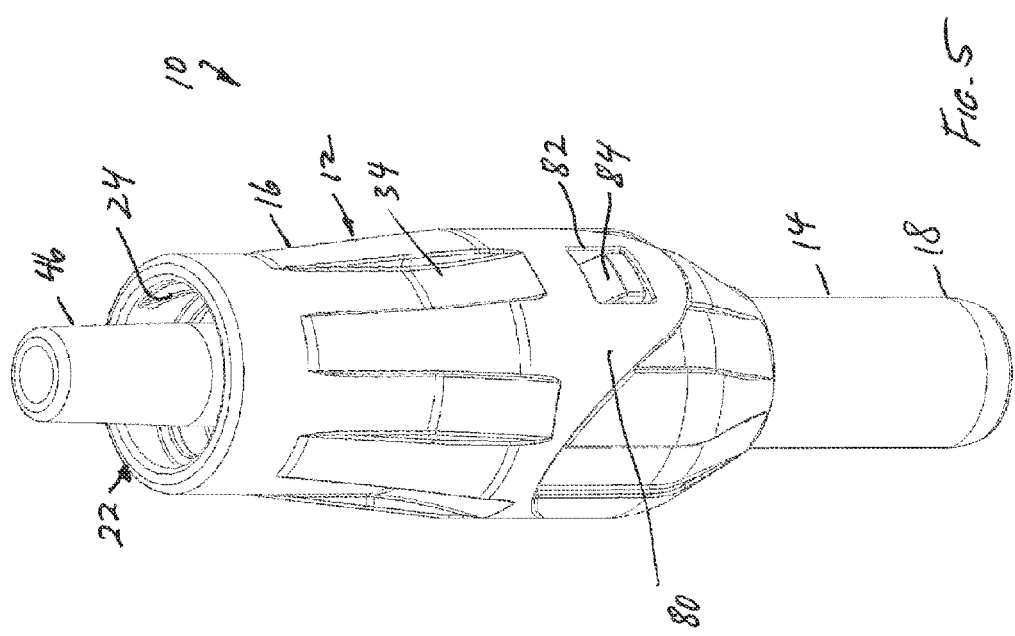

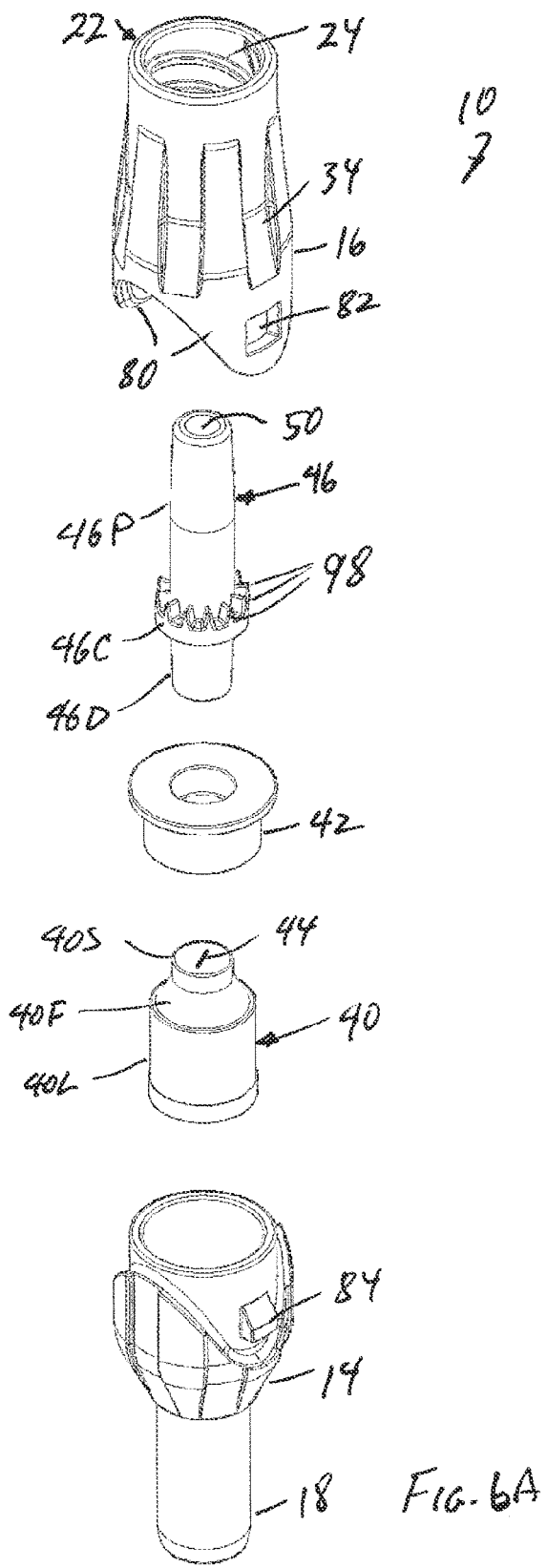

MALE REFLUX VALVE

CROSS-REFERENCE TO RELATED INVENTIONS

This application claims the benefit of provisional application Nos. 61/481,240, filed May 1, 2011, and 61/559,821, filed Nov. 15, 2011, the disclosures of each of which are hereby incorporated by reference herein.

BACKGROUND OF THE INVENTION

Field of the Invention

This invention relates to Luer activated devices. More particularly, invention relates to a male reflux valve for connection to a female Luer device and operable to allow fluid flow therethrough when connected thereto and to preclude reflux of fluid upon disconnection.

Description of the Background Art

Presently there exist numerous types of male reflux valves for intravenous (IV) lines, containers and the like that include an internal check valve that remains closed against a valve seat in its natural state to preclude fluid flow through the valve. When accessed by a device, the check valve is moved to a compressed state to unseat the check valve from the valve seat and allow bidirectional fluid flow through the valve. Upon disconnection of the access device, the check valve returns to its natural state to reseat itself against the valve seat thereby once again precluding fluid flow through the valve. Importantly, a male reflux valve connected to the IV line, container or the like precludes fluid from escaping therefrom unless and until it is accessed by an access device having the corresponding female Luer connection. Once accessed by the access device having the corresponding female Luer connection, fluid is allowed to flow bi-directionally through the valve out of the IV line, container or the like or into the IV line into the access device, container or the like from the access device.

Male reflux valves have been in widespread use in the medical industry, most commonly as ports in IV lines. More specifically, at their distal end, medical male reflux valves are typically configured with a tube end for fluid-tight connection into the IV line and a male Luer taper connection at their proximal end allowing connection thereto by the access device having a corresponding female Luer taper connection.

Typical male Luer taper connections may either comprise a Luer slip connection or a Luer lock connection. Luer slip connections comprise a Luer slip taper to achieve a press-fit slip connection between the male Luer slip taper of the male reflux valve and the corresponding female Luer slip taper of the access device. Male Luer lock connections include internal threads that threadably receive a corresponding tabbed hub on the female Luer lock connection of the access device. The Luer taper connections often conform to the industry standards specified in ISO 594, the disclosure of which is hereby incorporated by reference herein. Typical access devices include swabable valves of IV lines and other instruments having a female Luer connection that may be quickly connected to the male Luer connection of the male reflux valve.

Prior art patents on swabable valves owned by the assignee of this application are disclosed in U.S. Pat. Nos. 6,651,956 and 6,036,171, the disclosures of which are hereby incorporated by reference herein. Patents on prior a male reflux valves owned by the assignee of this application include U.S. Pat. Nos. 6,299,132, 6,543,745 and 6,609,696, the disclosures of each of which are hereby incorporated by reference herein.

It is desirous for the design of the male reflux valves is such that it promotes assembly by automated equipment during manufacture. Unfortunately, prior art male reflux valves are not easily assembled during their manufacture.

Therefore, an object of this invention to provide an improvement which overcomes the aforementioned inadequacies of the prior art devices and provides an improvement which is a significant contribution to the advancement of the reflux valve art.

Another object of this invention is to provide a male reflux valve having a design that is capable of being automatically assembled by automated assembly equipment during manufacture, thereby reducing the costs of manufacturing.

Another object of this invention is to provide a male reflux valve having an elastomeric valve element that is operatively positioned in the distal body portion and then retained into position by a core inserted into the distal body portion.

Another object of this invention is to provide a male reflux valve having a cannula-shaped actuator that is reciprocably and rotatably retained within the proximal body portion to open and close the valve element upon engagement and disengagement by an access device. Another object of this invention is to provide a male reflux valve that includes an anti-rotation feature to preclude rotation of the actuator as it is initially engaged by the access device or as the access device is initially being disengaged, thereby precluding an initial twisting torque being applied to the valve element as it is initially engaged or disengaged by the actuator.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purposes of summarizing this invention, the invention comprises a male reflux valve having a body composed of a distal body portion to be connected to an IV line, container or the like to preclude fluid from escaping therefrom unless and until the proximal body portion of the valve is accessed by an access device, whereupon fluid is allowed to flow bi-directionally through the valve out of the IV line, container or the like into the access device or out the access device into the IV line, container or the like.

The male reflux valve further comprises an elastomeric valve element that is operatively positioned in the distal body portion and then retained into position by a core inserted into the distal body portion. A cannula-shaped actuator is reciprocably and rotatably retained within the proximal body portion. The actuator is retained in the proximal body portion by a retainer wall positioned inside of the proximal body portion.

In valve's "closed" state, the valve element is positioned fully proximally in sealing engagement with the core, thereby preventing reflux of fluid is blocked (i.e., checked) from flowing through the valve. In the valve's "opened"

state upon engagement by an access device, the valve element is forced distally by the actuator and unseals itself from the core. Fluid is then allowed to flow through the valve. Upon removal of the access device, the valve element returns to its "closed state" and once again checks any flow of fluid through the valve.

Other embodiments of the male reflux valve of the invention include anti-rotation features to preclude rotation of the actuator as it is initially engaged by the access device and as the access device is initially being disengaged, thereby precluding an initial twisting torque being applied to the valve element as it is initially engaged or disengaged by the actuator.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be greatly appreciated by those skilled in the art that the conception and the specific embodiment disclosed may be readily utilized as a basis for modifying or designing other methods for carrying out the same purposes of the present invention. It should also be realized by those skilled in the art that such equivalent methods do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a perspective view of the first embodiment of the male reflex valve of the invention;

FIG. 5 is a perspective view of a second embodiment of the male reflux valve of the invention;

FIG. 6A is an exploded perspective view of the second embodiment of the male reflux valve of the invention showing the internal components thereof;

Similar reference characters refer to similar parts throughout the several views of the drawings.

DETAILED DESCRIPTION OF THE PREFERRED EMBODIMENT

Figure 2A:
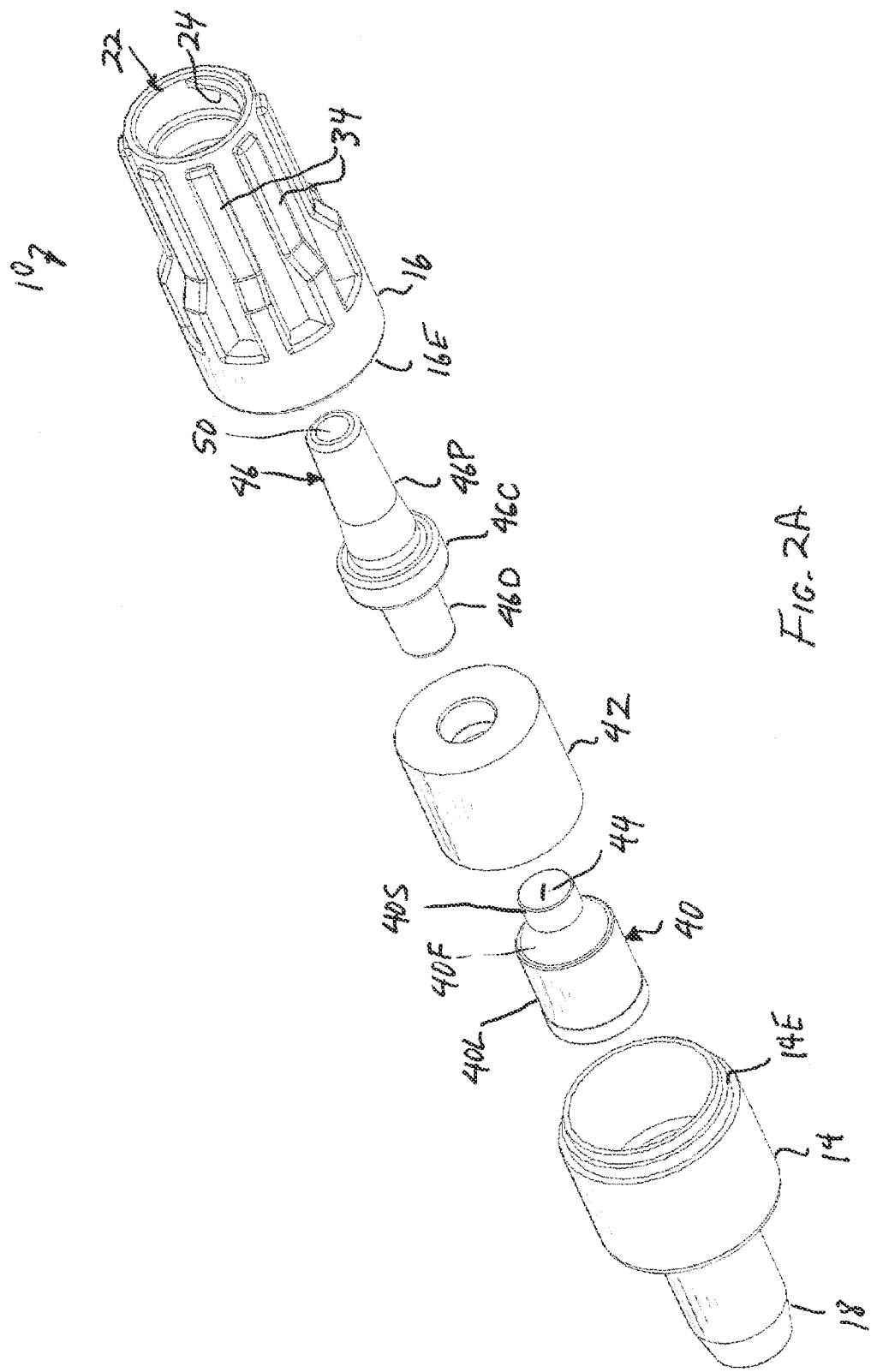
FIG. 2A is an exploded perspective view of the first embodiment of the male reflux valve of the invention showing the internal components thereof.

As shown in FIG. 1, the first embodiment of the male reflux valve 10 of the invention comprises a body 12 composed of a distal body portion 14 to be connected to an IV line, container or the like and a proximal body portion 16 to be accessed by an access device. The distal body portion 14 of the valve 10 is configured to be connected to the IV line, container or the like to preclude fluid from escaping therefrom unless and until the proximal body portion 14 of the valve 10 is accessed by an access device, whereupon fluid is allowed to flow bi-directionally through the valve 10 out of the IV line, container or the like into the access device or out the access device into the IV line, container or the like.

Without departing from the spirit and scope of this invention, it shall be understood that the distal body portion 14 may be configured as necessary for connection to the IV line, container or the like. Such connections may include without limitation, an integral connection wherein the distal body portion 14 is integrally formed with the IV line, container or the like, a permanent connection wherein the distal body portion 14 is welded or adhered to the IV line, container or the like or a removable or semi-removable connection wherein the distal body 14 is snapped into or onto, inserted into or onto or locked into or onto the IV line, container or the like.

As shown in FIG. 1, the preferred configuration of the distal body portion 14 comprises a tube-end connection 18 having a reduced diameter to be inserted into the end of a tube of an IV line and achieve a fluid-tight connection with the IV line.

The proximal body portion 16 of the body 12 of the male reflux valve 10 is configured to be accessible by the access device. Without departing from the spirit and scope of this invention, it shall be understood that the proximal body portion 16 may be configured as necessary for connection to the access device. Such connections may include without limitation, a removable or semi-removable connection wherein the access device is removably snapped into or onto, inserted into or onto or locked into or onto the proximal body portion 16.

The preferred configuration of the proximal body portion 16 comprises a male connection 22 for connection to the access device having a female connection. More preferably, the male connection 22 comprises a male taper such as either a male slip connection having a slip taper to achieve a press-fit slip connection with the corresponding female slip taper of the access device or a male lock connection having internal threads 24 that threadably receive a corresponding female lock connection of the access device. As shown in FIG. 1, most preferably the male connection 22 comprises a male lock connection with internal threads 24 that is configured and dimensioned to be removably connected to tabbed hub of a female lock connection of the access device, for example, a swabable female lock port of an IV bag. More preferably, the internal threads 24 of the male connection 22 are configured and dimensioned to threadably receive a corresponding female lock connection of the access device that meets the ISO standards for female Luer connections.

A plurality of longitudinal ridges 34 are preferably formed along the length of the proximal body portion 16 to allow a person to more easily grip the valve 10 while the access device is being connected thereto.

The distal body portion 16 and the proximal body portion 18 comprise mating annular edges 16E and 18E respectively, allowing the two body portions 16 and 18, once their components are assembled therein, to be connected together by means of a weld, adhesive or the like to form a fluid-tight connection between the two body portions 16 and 18.

Figure 2B:
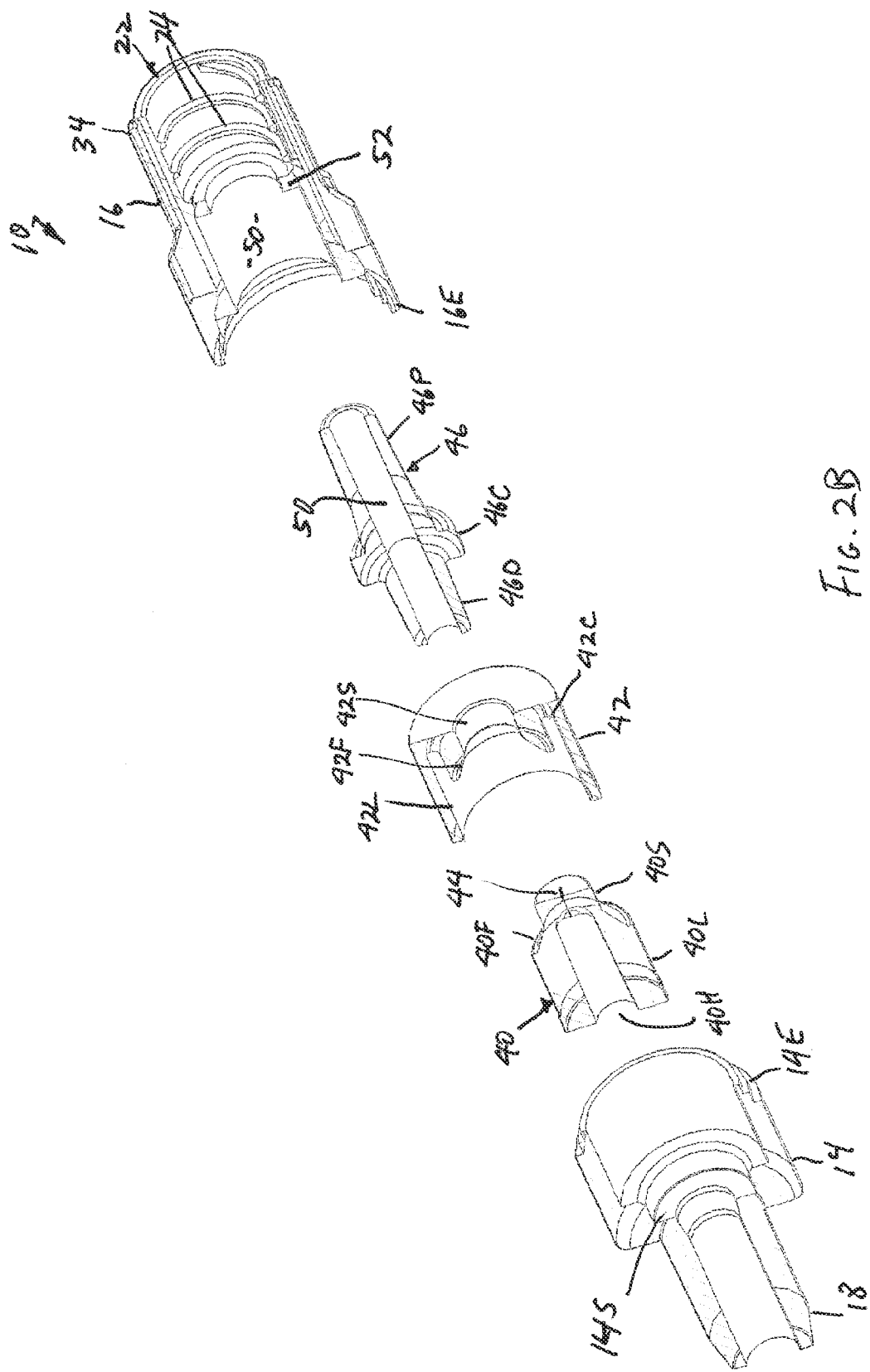
FIG. 2B is a cross-sectional view of FIG. 2A.

FIGS. 2A and 2B are exploded views of the first embodiment of the male reflux valve 10 of the invention showing the internal components thereof. More specifically, the male reflux valve 10 further comprises an elastomeric valve element 40 that is operatively positioned within a stopped seat 14S formed in the distal body portion 14 and then retained into position into sealing engagement with the stepped seat 14S by a core 42 inserted into the distal body portion 14.

The valve element 40 comprises a larger-diameter circular cylindrical portion 40L and a smaller-diameter circular cylindrical portion 40S joined at a frustoconical portion 40F. Correspondingly, the lumen of the core 42 comprises larger-diameter circular cylindrical portion 42L and a smaller-diameter circular cylindrical portion 42S joined at a frustoconical portion 42F. The frustoconical proximal end 40F of the valve element 40 fits into and therefore forms a seal with the corresponding frustoconical portion 42F of the core 42.

The valve element 40 includes a blind hole 40H. A slit 44 is formed at the end of the blind hole 40H through the smaller-diameter portion 40S. The slit 44 may comprise a normally-closed slit that is closed in its natural state (removed from the core 42) or a normally-opened slit that is opened in its natural state (removed from core 42). The blind hole 40H extending through the larger-diameter portion 40L and the frustoconical portion 40F of the valve element 40 allows the valve element 40 to collapse distally when forced distally.

Preferably, the dimensions of the frustoconical portion 42F (and optima of the smaller diameter portion 42S) of the core 42 are appreciably less than the dimensions of the frustoconical portion 40F (and of the smaller diameter portion 40S) of the valve element 40 such that the frustoconical portion 40F (and the smaller diameter portion 40S) of the valve element 40 are slightly compressed when positioned within the frustoconical portion 42F (and the smaller diameter portion 42S) of the core 42, thereby assuring that the slit 40S is held closed. Also preferably, the length of the larger diameter portion 40L of the valve element 40 is slightly greater than the length of the lumen of the core 42 such that when the valve element 40 is assembled into the lumen of the core 42 and seated in the stepped seat 14S, the valve element 40 is under longitudinal compression to form a seal between the mating frustoconical portions 40F and 42F.

More preferably, the valve element 40 and lumen of the core 42 are configured to operate substantially similar to the valve stem shown and described in U.S. Pat. No. 6,651,956 incorporated by reference above.

A cannula-shaped actuator 46 is reciprocably and rotatably retained within a generally circular cylindrical longitudinal bore 48 of the proximal body portion 16. The actuator 46 comprises a generally circular cylindrical small-diameter distal portion 46D, a generally circular cylindrical large-diameter center portion 46C and a generally circular cylindrical small-diameter proximal portion 46P, with a longitudinal bore 50 extending therethrough. The inner diameter of the longitudinal bore 48 is slightly greater than the outer diameter of the large-diameter center portion 46C allowing the actuator 46 to reciprocate longitudinally therein. Further, the generally circular cylindrical configurations of the longitudinal bore 48 and the large-diameter center portion 46C allows the actuator 44 to rotate within the longitudinal bore 48.

A retainer wall 52 extends radially inwardly in the longitudinal bore 48 to retain the actuator 46 in the proximal body portion 16. Preferably the retainer wall 52 is positioned distal of the internal threads 24 formed along the lumen of the longitudinal bore 48, thereby allowing significant distal travel of the actuator 46 longitudinally within the bore 48 from the point its large-diameter center portion 64C engages against the distal side of the retainer wall 52.

Figure 3:
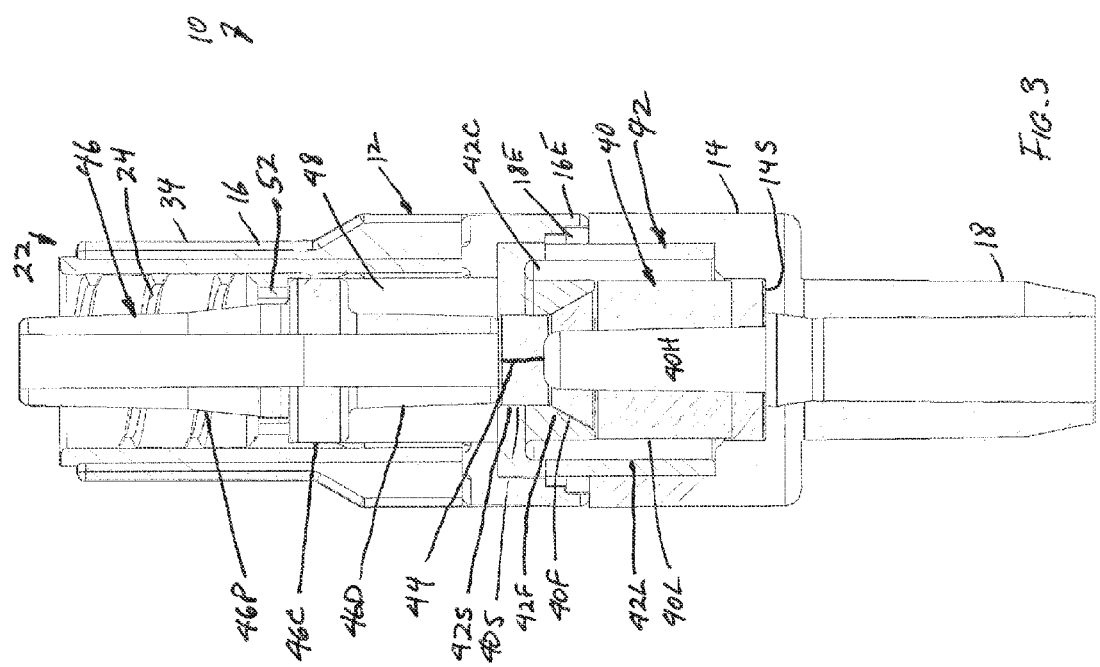
FIG. 3 is a longitudinal cross-sectional view of the first embodiment of the male reflux valve of the invention in its "closed" natural state.
Figure 4:
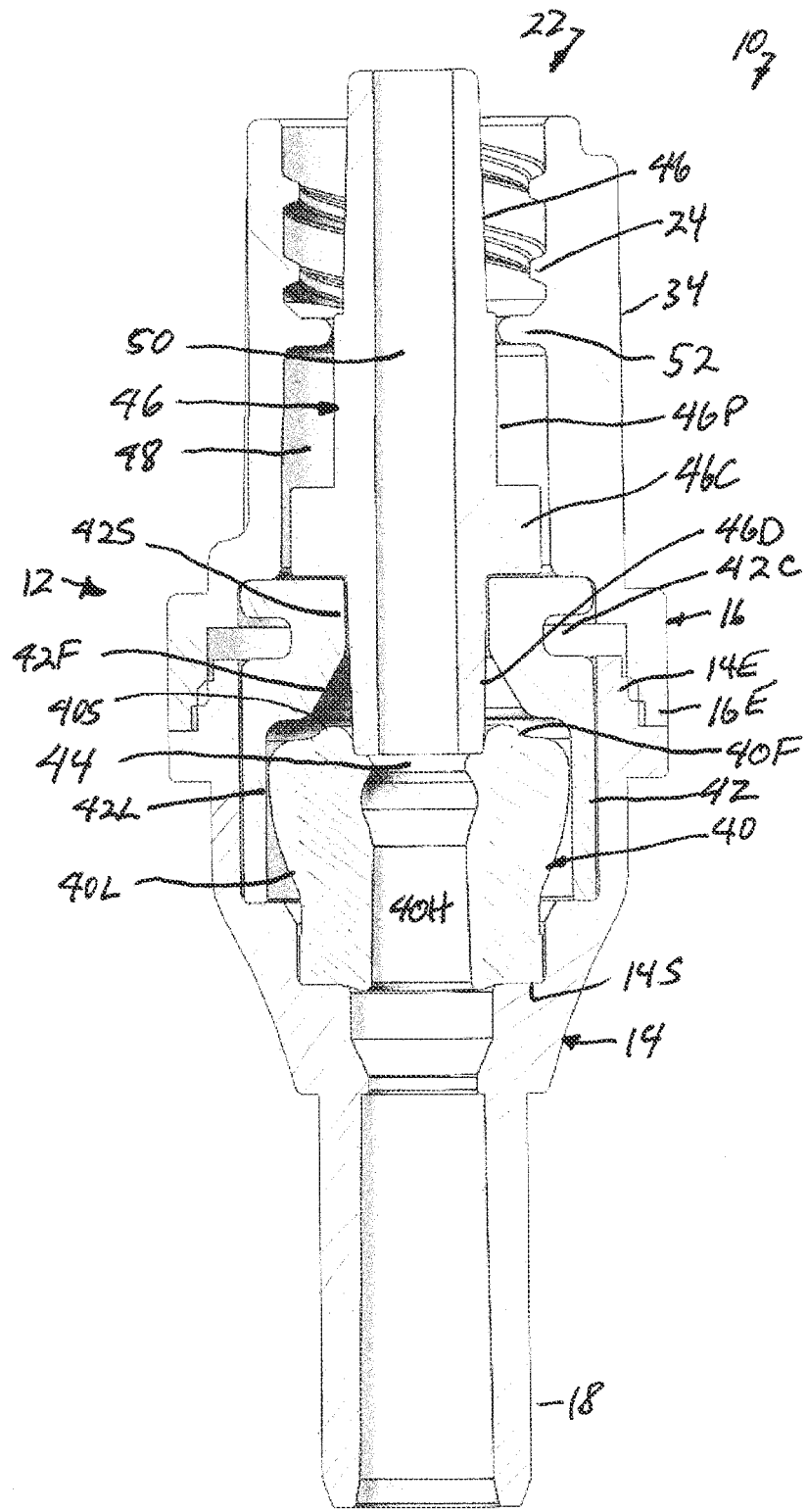
FIG. 4 is a longitudinal cross-sectional view of the first embodiment of the male reflux valve of the invention in its "opened" state once accessed by an access device.
Figure 6B:
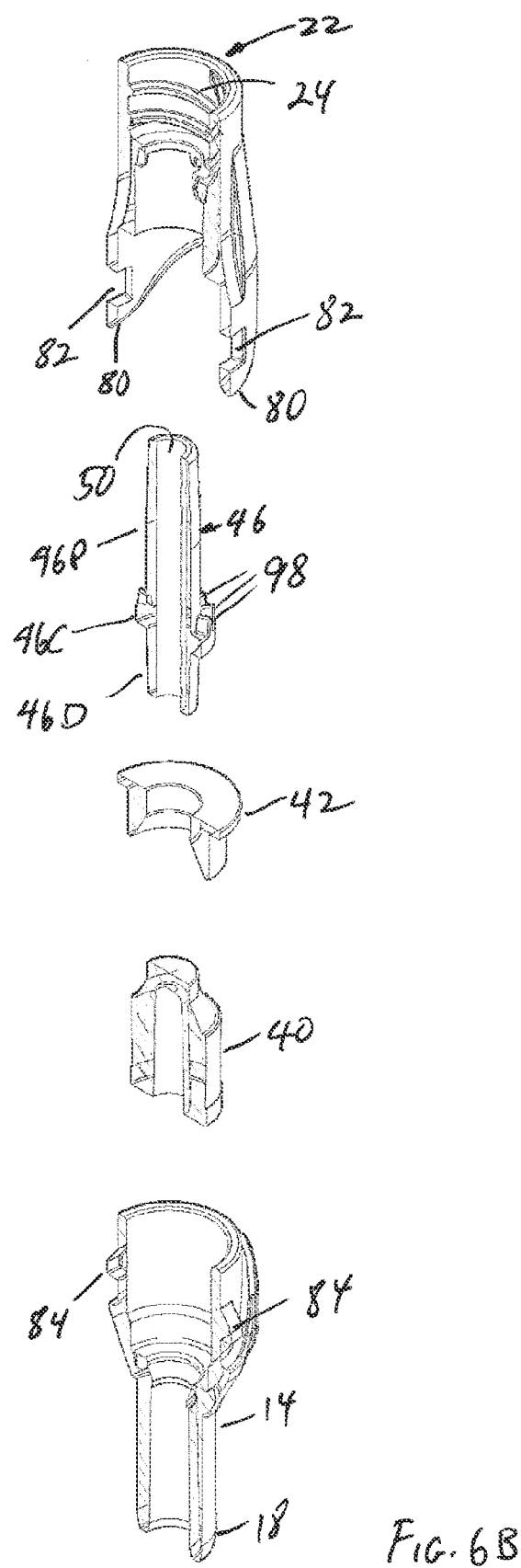
FIG. 6B is a cross-sectional view of FIG. 6A.

FIG. 3 is a longitudinal cross-sectional view of the male reflux valve of the invention in its "closed" state with the valve element 40 positioned fully proximally within the lumen of the core 42 whereas FIG. 4 is a longitudinal cross-sectional view of the valve in its "opened" state with the valve element 40 having been forced distally by the actuator 46. Preferably, the inside diameter of the larger diameter portion 42L of the lumen of the core 42 is appreciably greater than the outside diameter of the larger diameter portion 40L of the valve element 40 to allow room for lateral expansion of the larger-diameter portion 40L upon longitudinal compression of the valve element 40.

As shown in FIG. 4, the proximal end of the core 42 may include cut-outs 42C to reduce material costs.

As shown in FIG. 3, in the "closed" natural state of the male reflux valve 10, the slit 44 of the valve element 40 is sealed, the respective frustoconical portions 40F and 42F of the valve element 40 and core 42 are sealed and the distal end of the larger-diameter portion 40L of the valve element 40 is sealed in the stepped seat 14S of the distal body portion 14. Reflux of fluid from the distal body portion 14 to the proximal body portion 16 is therefore blocked (i.e., checked).

As shown in FIG. 4, as an access device is being connected to the male connection 22, the actuator 46 is forced distally within the bore 48. The lip of the distal end of the actuator 46 circumscribes the slit 44 of the valve element 40 and forms a seal therearound. Further distal movement of the actuator 46 then compresses the valve element 40 and forces its smaller-diameter portion 40S to move distally out of the small-diameter portion 42S of the core 42 whereupon the smaller-diameter portion 40S is no longer under compression and the slit 44 opens. Upon opening of the slit 44, a bi-directional fluid path is created in the valve 10 allowing fluid flow to and from the access device. Notably, despite the valve being opened, the lip of the distal portion 46D of the actuator 46 maintains a seal with the valve element 40 and the bottom of the larger-diameter portion of the valve element 40 maintains a seal with the stepped seat 14S, thereby assuring that no fluid escapes into the dead space between the valve element 40 and the core 42 while the valve 10 remains open.

Upon removal of the access device, the inherent resiliency of the valve element 40 causes it to return to its "closed" natural state as shown in FIG. 3 with the actuator 46 then being urged in its fully proximal position. Importantly, at all times while the valve 10 is opening or closing, the fluid flow path extends only through the longitudinal bore 50 of the actuator 46, the longitudinal bore 48 of the valve element 40 and that portion of the longitudinal bore of the tube end connection 18 into the tube connected thereto, thereby achieving minimal displacement of fluid.

Notably, the design of the male reflux valve 10 of the invention facilitates automated assembly. Specifically, the valve element 40 may be inserted into the distal body portion 14 and then the core 42 may be inserted in the body portion 14. Alternatively, the valve element 40 may be inserted into the core 42 and the valve element 40/core 42 assembly inserted into the distal body portion 14. The actuator 46 may be inserted into the proximal body portion 16 and then actuator 46/proximal body portion 16 assembly aligned with the distal body portion 14, mated together and then welded along edges 16E and 14E.

FIGS. 5-8 illustrate a second embodiment of the male reflux valve 10 of the invention that includes the added feature of precluding rotation of the actuator 46 as the male connection 22 is initially engaged by an access device, thereby precluding an initial twisting torque being applied to the valve element 40 as it is initially engaged by the actuator 46. The second embodiment also includes the added feature of the distal and proximal body portions 14 and 16 of the body 12 of the valve 10 snapping together during assembly. The remaining components of the second and third embodiments of the male reflux valve 10 of the invention are similar in design to those components already described above in relation to the first embodiment. Therefore, similarly-used reference numerals are used throughout FIGS. 5-8.

More particularly, the snap-together design feature of the second embodiment of the male reflux valve 10 of the invention is achieved by forming a pair of diametrically-opposed ears 80 extending distally from the proximal body portion 16, each having an opening 82. Correspondingly, the distal body portion 14 comprises a pair of diametrically-opposed tabs 84 extending radially therefrom. The tabs 84 are configured and dimensioned to fit into the corresponding openings 82 formed in the ears 80 thereby providing a snap-fit. As shown, the proximal surface of the tabs 84 may include a slight taper to facilitate assembly whereas the distal surface of the tabs 84 is preferably formed at a right angle to provide a more firm engagement of the tab 84 into the opening 82 after assembly.

Figure 7:
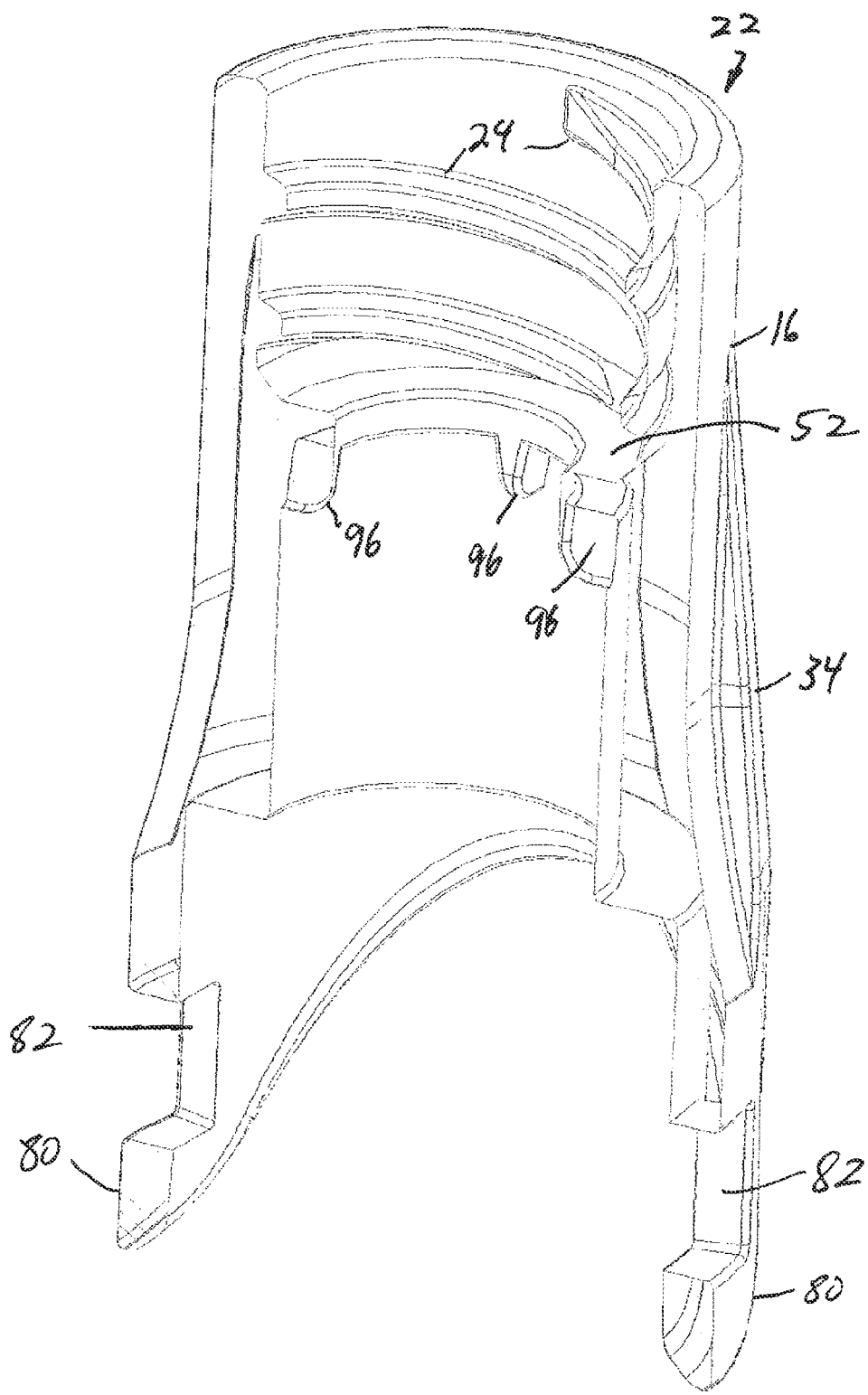
FIG. 7 is an enlarged cross-sectional perspective view of the proximal body portion of the second embodiment of the male reflux valve of the invention.
Figure 8:
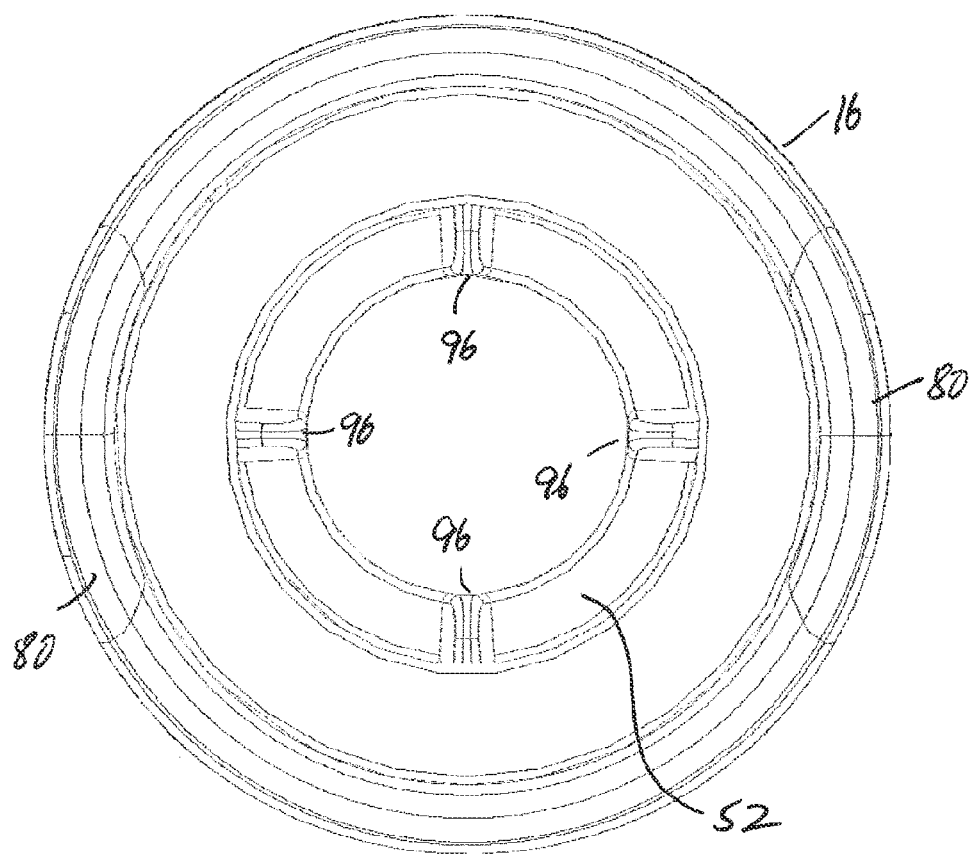
FIG. 8 is a distal end view of the proximal body portion of the second embodiment of the male reflux valve of the invention.

The anti-rotation feature of the second embodiment of the male reflux valve 10 of the invention comprises a plurality (e.g. four) equidistantly spaced radial teeth 96 extending distally from the retainer wall 52 of the proximal body portion 16 (see FIGS. 7 and 8). A plurality of uniformly spaced radial teeth 98 extend proximally from the increased-diameter center portion 46C of the actuator 46 in geared alignment with the teeth 96 extending distally from the retainer wall 52. The length of the teeth 96 and 98 are dimensioned to engage together when the actuator 46 is at rest in its fully proximal position (e.g., not being engaged by the access device) and to then disengage once the actuator 46 is engaged and moved slightly distally by the access device. Because initial rotation of the actuator 46 is precluded, the valve element 40 may be initially engaged by the actuator 46 without any twisting motion being imparted to it by the actuator 46. However, once the actuator 46 is moved slightly distally by the length of the teeth 96 and 98 upon engagement by the access device, the teeth 96 and 98 disengage from one another and the actuator 46 may then freely rotate relative to the proximal body portion 16.

Figure 9:
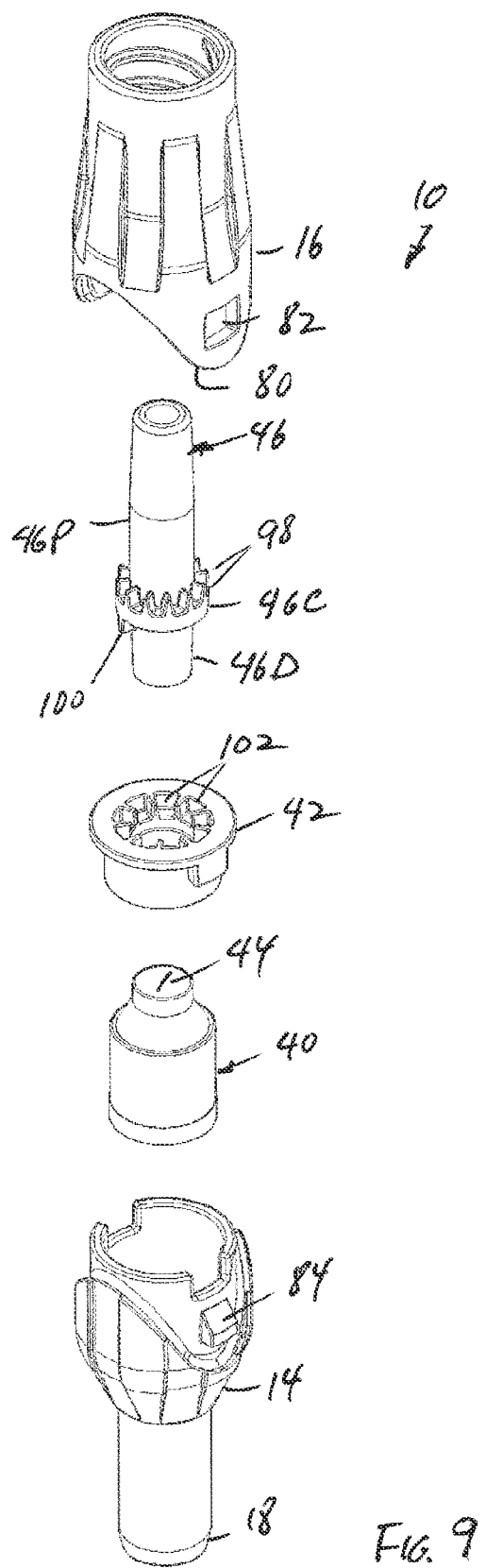
FIG. 9 is an exploded perspective view of the third embodiment of the male reflux valve of the invention showing the internal components thereof.
Figure 10:
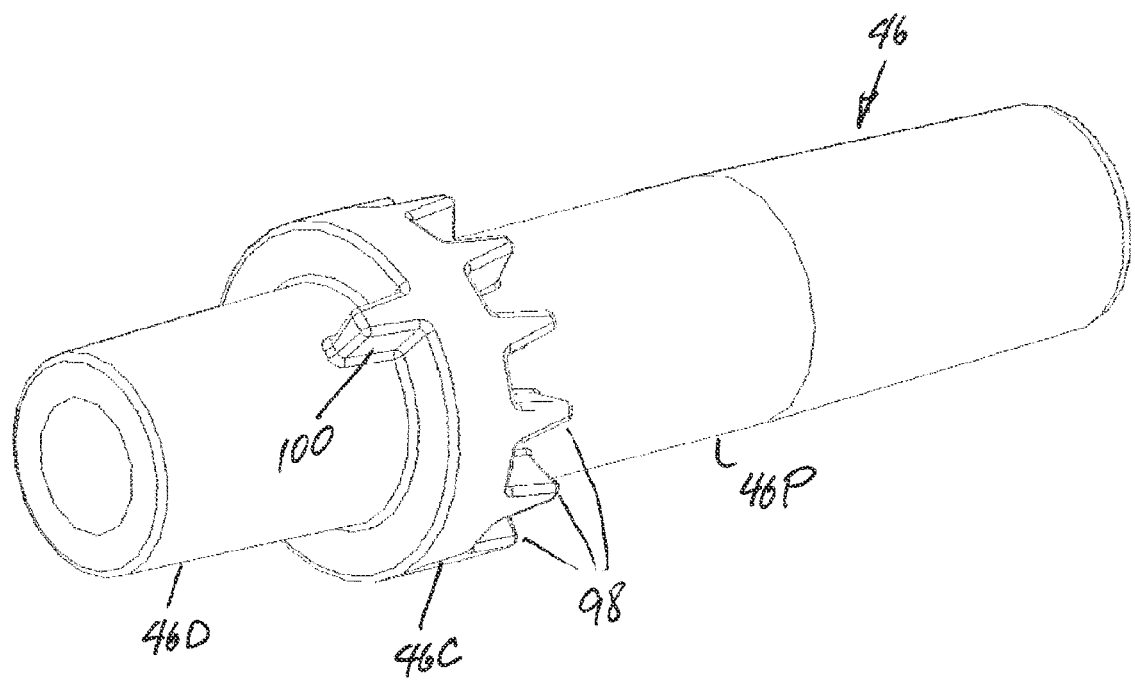
FIG. 10 is an enlarged perspective view of the actuator thereof.
Figure 11:
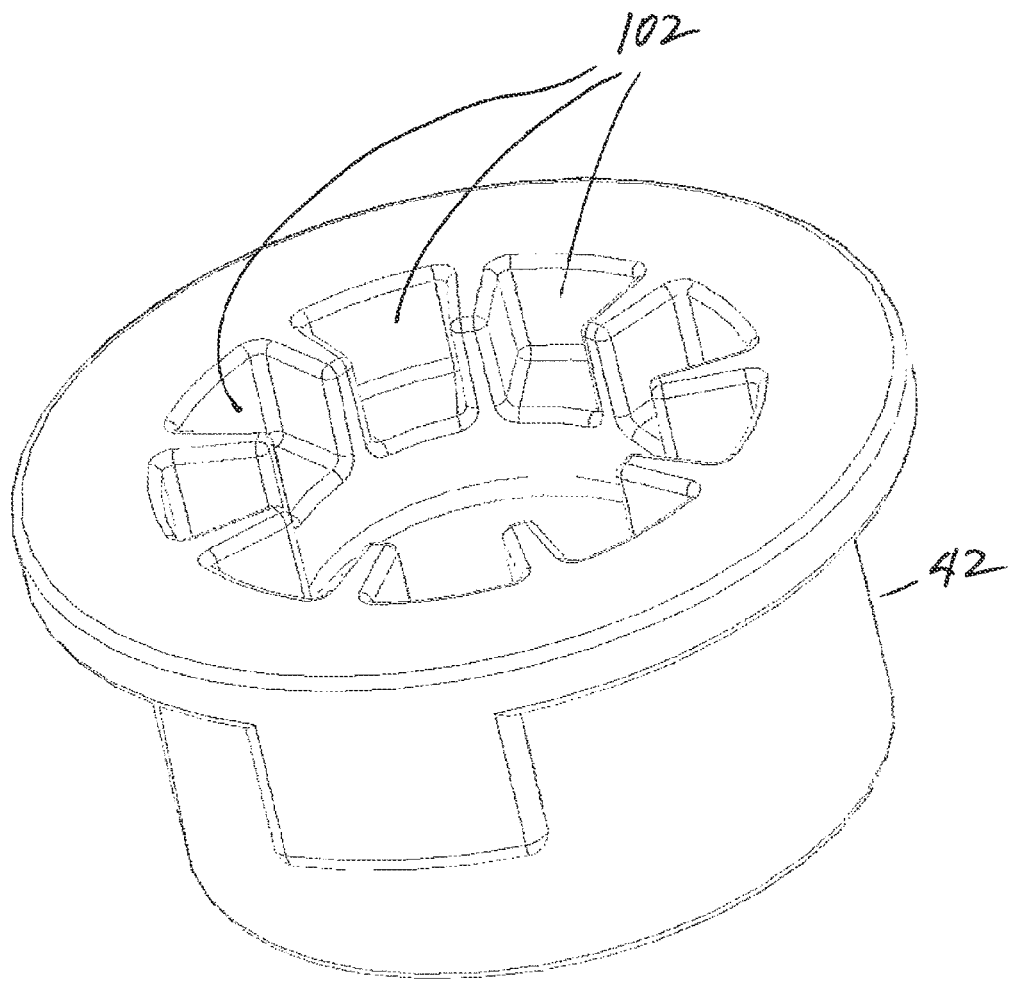
FIG. 11 is an enlarged perspective view of the core thereof.

The third embodiment of the valve 10 of the invention is shown in FIGS. 9-11 includes the added feature of precluding rotation of the actuator 46 as the fully-installed access device is initially removed from the male connection 22 of the valve 10, thereby precluding any twisting torque being applied to the valve element 40 upon initial disengagement. Many components of the third embodiment of the male reflux valve 10 of the invention are similar in design to those components already described above in relation to the second embodiment. Therefore, similarly-used reference numerals are used throughout FIGS. 9-11.

The anti-rotation feature of the third embodiment of the male reflux valve 10 of the invention comprises a plurality (e.g. two) diametrically-spaced radial teeth 100 extending distally from the diameter center portion 46C of the actuator 46 (see FIGS. 7 and 8). A plurality of uniformly spaced recesses 102 extend proximally from the proximal surface of the core 42 in geared alignment with the teeth 100 extending distally from the center portion 46C. The length of the teeth 100 is dimensioned to engage into the recesses 102 when the actuator 46 is in its fully distal position (e.g., being fully engaged by the access device) and to then immediately disengage once the actuator 46 is moved slightly proximally by the access device. Because rotation of the actuator 46 is precluded, it begins to initially move proximally away from the valve element 40 without any twisting motion being imparted to it by the actuator 46. However, once the actuator 46 is moved slightly proximally by the length of the teeth 100 as the access device starts t be removed, the teeth 100 disengage from the recesses 102 and the actuator 46 may then rotate relative to the valve element 40.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:
1. A male reflux valve comprising in combination:
   a body comprising a distal body portion and a proximal body portion, said proximal body portion having a male connection for connection to an access device having a female connection;
   an elastomeric valve element operatively positioned within said distal body portion, said valve element including a slit;
   a core operatively positioned within said distal body portion between said proximal body portion and said distal body portion to retain said valve element into sealing engagement with said distal body portion in an orientation with said slit facing proximally toward said proximal body portion; and
   an actuator reciprocably retained within a generally circular cylindrical longitudinal bore of the proximal body portion; said actuator comprising a small-diameter distal portion, a large-diameter center portion and a small-diameter proximal portion, with a longitudinal bore extending therethrough for fluid flow therethrough;
   a retainer wall extending radially inwardly within said proximal body portion to retain said center portion in said proximal body portion;
   said small-diameter distal portion being in engagement with said slit of said valve element to open said valve element when said proximal portion is engaged by the female connection of the access device, whereby moving said actuator distally causes a lip of said distal portion to open said slit and form a seal therearound to establish a bi-directional fluid path in the valve allowing fluid flow to and from the access device.
2. The male reflux valve as set forth in claim 1, further including a plurality of longitudinal ridges formed along the length of said proximal body portion.
3. The male reflux valve as set forth in claim 1, wherein said distal body portion and said proximal body portion comprise mating annular edges to be connected together to form a fluid-tight connection therebetween.

4. The male reflux valve as set forth in claim 1, wherein said valve element includes a blind hole with said slit formed at the end of said blind hole.

5. The male reflux valve as set forth in claim 1, wherein said valve element is slightly compressed when positioned within said core to close said slit.

6. The male reflux valve as set forth in claim 5, wherein said valve element forms a seal with said core when positioned within said core.

7. The male reflux valve as set forth in claim 1, wherein a distal end of said actuator compresses said valve element as said valve element moves distally whereupon said slit opens.

8. The male reflux valve as set forth in claim 7, wherein when said slit opens, fluid flows through said valve element and then through said actuator.

9. The male reflux valve as set forth in claim 8, wherein said valve element is composed of a resilient material to cause said valve element to return into sealing engagement with said core.

10. The male reflux valve as set forth in claim 1, wherein said distal and proximal body portions snap together during assembly, one including tabs and the other including ears with at least one opening in mating engagement.

11. The male reflux valve as set forth in claim 1, further including teeth disposed on said actuator that engage corresponding teeth disposed on said proximal body portion to preclude an initial twisting torque being applied to said valve element as said actuator is engaged by the access device.

12. The male reflux valve as set forth in claim 1, further including teeth disposed on said actuator that engage corresponding recesses disposed in said core to preclude an initial twisting torque being applied to said valve element as said actuator moves proximally upon initial removal of the access device.

* * * * *